(12) United States Patent
Zhu et al.

(10) Patent No.: US 10,869,948 B2
(45) Date of Patent: Dec. 22, 2020

(54) COMPOSITION OF COLLAGEN PEPTIDE AND ELASTIN PEPTIDE, METHOD OF PRODUCING THE SAME AND USE THEREOF

(71) Applicant: INFINITUS (CHINA) COMPANY LTD., Guangdong (CN)

(72) Inventors: Huawei Zhu, Guangdong (CN); Xiaoling Wang, Guangdong (CN); Liugang Ding, Guangdong (CN); Xiaolei Guo, Guangdong (CN); Yazhong Ge, Guangdong (CN)

(73) Assignee: INFINITUS (CHINA) COMPANY LTD., Guangdong (CN)

( * ) Notice: Subject to any disclaimer, the term of this patent is extended or adjusted under 35 U.S.C. 154(b) by 0 days.

(21) Appl. No.: 16/413,628

(22) Filed: May 16, 2019

(65) Prior Publication Data

US 2020/0222585 A1   Jul. 16, 2020

(30) Foreign Application Priority Data

Jan. 11, 2019   (CN) .......................... 2019 1 0036842

(51) Int. Cl.
| | |
|---|---|
| *A61L 27/24* | (2006.01) |
| *A61P 17/00* | (2006.01) |
| *A61L 27/36* | (2006.01) |
| *C07K 14/78* | (2006.01) |
| *C12N 9/76* | (2006.01) |
| *C12N 9/64* | (2006.01) |

(52) U.S. Cl.
CPC .......... *A61L 27/24* (2013.01); *A61L 27/3604* (2013.01); *A61L 27/3645* (2013.01); *A61L 27/3687* (2013.01); *A61P 17/00* (2018.01); *C07K 14/78* (2013.01); *C12N 9/6427* (2013.01); *C12N 9/6481* (2013.01)

(58) Field of Classification Search
CPC ..................................................... A61L 27/24
See application file for complete search history.

(56) References Cited

U.S. PATENT DOCUMENTS

| | | | | |
|---|---|---|---|---|
| 6,548,077 B1 * | 4/2003 | Gunasekaran | ............ | A61P 7/04 424/422 |
| 2003/0096409 A1 * | 5/2003 | Yasumoto | ............. | A61L 27/383 435/371 |
| 2003/0203008 A1 * | 10/2003 | Gunasekaran | ......... | C07K 14/78 424/442 |
| 2008/0118947 A1 * | 5/2008 | Yu | .......................... | C07K 14/78 435/68.1 |
| 2019/0276515 A1 * | 9/2019 | Bruno-Bonnet | ........ | A23L 33/17 |

FOREIGN PATENT DOCUMENTS

| | | | | | |
|---|---|---|---|---|---|
| WO | WO 2006/096027 | * | 9/2006 | .............. | C12P 21/00 |
| WO | WO 2015/012682 | * | 1/2015 | ............... | C07K 1/14 |

OTHER PUBLICATIONS

Ferraro et al., 2017, Collagen type I from bovine bone. Effect of animal age, bone anatomy and drying methodology on extraction yield, self-assembly, thermal behavior and electrokinetic potential, International Journal of Biological Macromolecules, 97: 55-66.*
McIntosh et al., 1962, The Effect of Papain Preparations on Beef Skeletal Muscle Proteins, 283-285.*
Mecham, 2008, Methods in Elastic Tissue Biology: Elastin Isolation and Purification, Methods, 45(1): 32-41.*
Sivadas et al., 2011, Inhalable, bioresponsive microparticles for targeted drug delivery in the lungs, Journal of Pharmacy and Pharmacology, 63: 369-375.*
Ahmad et al., 2010, Extraction and characterization of pepsin-solubilised collagen from the skin of unicorn leatherjack (*Aluterus monocerous*), Food Chemistry, 120: 817-824.*
Ferraro et al., 2016, The "sisters" alpha-helices of collagen, elastin and keratin recovered from animal by-products: Functionality, bioactivity and trends of application, Trends in Food Science & Technology, 51: 65-75.*
Daamen et al., 2005, Isolation of Intact Elastin Fibers Devoid of Microfibrils, Tissue Engineering, 11(7/8): 1168-1176.*

* cited by examiner

*Primary Examiner* — Amber D Steele
(74) *Attorney, Agent, or Firm* — Yue (Robert) Xu; Apex Attorneys at Law, LLP

(57) ABSTRACT

Disclosed is a composition of a collagen peptide and an elastin peptide, method of producing the same and use thereof. The composition of the present disclosure consists of a collagen peptide and an elastin peptide; the collagen peptide is prepared by enzymatic hydrolysis of a collagen material with pepsin or trypsin, and the elastin peptide is prepared by enzymatic hydrolysis of an elastin material with papain and/or protease Protamex. In the present disclosure, an elastin peptide and a collagen peptide with molecular weight in a specific range are prepared by specific processes, and the composition composed of the two at a suitable ratio can simultaneously and significantly increase the amount of the elastin and collagen in a damaged skin in a small usage amount, and significantly increase the content of hyaluronic acid and hydroxyproline while decrease the content of MMP3, meanwhile, inhibit skin inflammatory factors.

4 Claims, No Drawings

COMPOSITION OF COLLAGEN PEPTIDE AND ELASTIN PEPTIDE, METHOD OF PRODUCING THE SAME AND USE THEREOF

CROSS REFERENCE TO RELATED APPLICATIONS

This application claims the priority of Chinese Patent Application No. 201910036842.5, filed on Jan. 11, 2019, and the disclosures of which are hereby incorporated by reference.

FIELD

The present disclosure relates to the field of food and medicine technology, in particular to a composition of a collagen peptide and an elastin peptide, method of producing the same and use thereof.

BACKGROUND

Elastin is a protein constituting elastic fiber and widely distributed in various tissues and organs in a living body, and it is mainly present in elastic tissues such as cervical ligament, blood vessel, lung, and skin. Such tissues not only require elasticity, but indispensably need tensile strength. Elastin plays an important role in the formation and maintenance of the structure of tissues. Elastin is rich in hydrophobic amino acids such as glycine, alanine and proline. In the process of biosynthesis of elastin, its precursor tropoelastin forms amino acids, desmosine, and isodesmosine through the function of lysyl oxidase, and interferes the cross-linked structure composed of four lysine residues. Therefore, elastin helps to maintain the stability and elasticity of the tissue structure.

With advancing age, the amount of elastin in our skin is reduced, which in turn reduces the network support needed to maintain firming skin. As a result, the skin becomes slack and the outline becomes loose. After 25 years of age, our body will stop producing elastin, and the elastin in the skin continues to be lost, and the skin begins to relax and have fine lines and other aging phenomena. Scientific studies have confirmed that the age of the skin is determined by the percentage of elastin, and only elastin can provide and maintain the two-dimensional elasticity of the skin.

Collagen and elastin are two proteins located in the dermal layer beneath the epidermis of the skin. Fibroblasts are the special cells in connective tissue which produce these two substances. The "basal skin" formed by collagen and elastin is the epidermis supported by collagen. Collagen increases skin elasticity, lifts firmness, and provides activity. These two proteins retain moisture, nourish the skin, moisturize, smooth the skin and prevent wrinkles.

Many people think that the key to maintain skin youth is to supplement collagen. In fact, elastin is more important. Elastin plays a role of a rubber band in the skin, giving the skin an ability to stretch and fold. It functions as the spring in the mattress, which is responsible for maintaining the elasticity of supporting the skin. Therefore, elastin plays an important role in maintaining skin elasticity. Elastin determines the elasticity and softness of the skin, and has a function of preventing aging and promoting regeneration for the physiological aging process of the skin caused by physical and chemical factors such as light. If a skin care product contains both elastin and collagen, it will be very good for keeping the skin young, delicate and elastic.

Elastin was used for cosmetic purposes long time ago, and a bovine neck ligament was used as the raw material for cosmetics. In recent years, with the discovery of BSE and poultry infectious diseases, the safety of the material has been questioned, so it is urgent to seek alternative raw materials.

Under such a background, people have explored a method for producing an elastin peptide by using bovine ligament, bovine cardiac tube, bonito arterial ball, and porcine cardiac large artery as raw materials, achieving the purpose of beauty by oral administration and skin care. However, due to the process preparation of elastin peptides and the popular factors, the cost is high, and the premise of increasing the content of elastin is to consume a sufficient amount of elastin peptide, which will undoubtedly increase the consumer's cost. In addition, in addition to skin relaxation caused by age, skin inflammation caused by external environment is also a major factor affecting aging. How to make elastin play its role efficiently and inhibit skin inflammation is a research topic with broad economic value.

SUMMARY

In view of the above, an object of the present disclosure is to provide a composition of a collagen peptide and an elastin peptide and method of producing the same. The composition has a synergistic effect and can significantly increase the contents of elastin and collagen.

Another object of the present disclosure is to provide a composition of a collagen peptide and an elastin peptide and method of producing the same. The composition can significantly increase the content of hyaluronic acid and hydroxyproline and decrease the content of MMP3 simultaneously.

Another object of the present disclosure is to provide a composition of a collagen peptide and an elastin peptide and method of producing the same. The composition can significantly inhibit skin inflammatory factors, thereby achieving the purpose of inhibiting skin inflammation.

Another object of the present disclosure is to provide a use of the above composition in the manufacture of foods and/or medicaments.

In order to achieve the above object, the present disclosure provides the following technical solutions.

A composition consists of a collagen peptide and an elastin peptide; the collagen peptide is prepared by enzymatic hydrolysis of a collagen material with pepsin or trypsin, and the elastin peptide is prepared by enzymatic hydrolysis of an elastin material with papain and/or protease Protamex.

Preferably, the mass ratio of the collagen peptide to the elastin peptide is (1.6-3.2):(0.075-0.2); more preferably (1.6-2.4):0.1; in a specific embodiment of the present disclosure, the mass ratio of the collagen peptide to the elastin peptide is 1.6:0.1 or 2.4:0.1, such as 3.2 g of collagen peptide and 0.2 g of elastin peptide, or 4.8 g of collagen peptide and 0.2 g of elastin peptide.

In a specific embodiment of the present disclosure, the collagen material is selected from cod, and the elastin material may be selected from one or more materials with high elastin content such as bovine ligament, bovine cardiac tube, bonito arterial ball, and porcine cardiac large artery.

In addition, the present disclosure also provides a method of producing the composition, comprising:

performing enzymatic hydrolysis of the collagen material with pepsin or trypsin, passing the enzymatic hydrolysate through a 1 to 2 μm filter membrane, and subjecting the filtrate to spray drying to obtain the collagen peptide;

removing fats and impurities on the surface of the elastin peptide material, performing enzymatic hydrolysis of the elastin peptide material with papain and/or protease Protamex, passing the enzymatic hydrolysate through a 0.45 to 1 μm filter membrane, and subjecting the filtrate to spray drying to obtain the elastin peptide; and mixing the collagen peptide and the elastin peptide to obtain the composition.

Further, the method comprises:

drying and pulverizing the collagen material, adding water and pepsin or trypsin 1% amount of the collagen material to perform enzymatic hydrolysis, passing the enzymatic hydrolysate through a 1 to 2 μm filter membrane, and subjecting the filtrate to spray drying to obtain the collagen peptide;

removing fats and impurities on the surface of the elastin peptide material by soaking the elastin peptide material with a NaOH solution, washing and mincing the material, adding water and adjusting pH to 7.5 to 8.5, adding papain and/or protease Protamex 0.4-0.8% amount of the elastin peptide material to perform enzymatic hydrolysis, filtering the enzymatic hydrolysate by a plate and frame filter and a 0.45 to 1 μm filter membrane, and subjecting the filtrate to spray drying after concentrating to obtain the elastin peptide; and mixing the collagen peptide and the elastin peptide to obtain the composition.

In a specific embodiment of the present disclosure, the method comprises:

chopping the collagen peptide material and drying in an 80° C. oven for 12 hours, pulverizing into powders by a pulverizer, adding water 20 to 30 times of the powders, heating the resulting solution to a temperature of 60° C.±5° C., adding pepsin/trypsin 1% amount of the powders into the solution to perform enzymatic hydrolysis for 4 to 8 hours, increasing the temperature to 80±5° C. and maintaining the temperature for 0.5 to 1 hour, inactivating the enzyme, passing the enzymatic hydrolyzate through a 1 to 2 μm filter membrane, maintaining the temperature at 55±5° C., and subjecting the filtrate to spray drying to obtain the collagen peptide;

washing the elastin peptide material, adding 0.5% NaOH solution to soak the material at 40 to 50° C. for 1 to 2 hours to remove fats and impurities on the surface, washing the material until neutral, draining and mincing to obtain a crude extract of elastin, adding water 2 to 4 times of the elastin peptide material and adjusting pH to 7.5 to 8.5, adding papain and/or protease Protamex 0.4 to 0.8% amount of the elastin peptide material, maintaining the temperature at 60° C. for 6 to 8 hours, increasing the temperature to 90° C., maintaining the temperature for 0.5 to 1 hour, inactivating the enzyme, filtering the resultant by a plate and frame filter and a 0.45 to 1 μm filter membrane, collecting the filtrate to obtain a solution of elastin peptide, subjecting the solution to spray drying after concentrating to obtain the elastin peptide; and mixing the collagen peptide and the elastin peptide to obtain the composition.

The collagen peptide obtained by the method of the present disclosure has a molecular weight of 2000 Da to 6000 Da as determined by high-performance size exclusion chromatography. The elastin peptide has a molecular weight of 300 Da to 2000 Da by high performance gel exclusion chromatography. The composition made of the two at the ratio of the present disclosure, compared with a single protein peptide, in the same use amount, can significantly increase the content of elastin and collagen in the skin of the mouse model with damaged skin, and significantly increase the content of hyaluronic acid and hydroxyproline and decrease the content of MMP3. In another word, the composition of the present disclosure, using less amount of elastin peptide and collagen peptide, can reach or exceed the effects in various aspects of the elastin peptide or collagen peptide in an larger use amount. In addition, the present disclosure establishes control groups using different production processes, and none of the control groups can achieve the excellent effects of the present disclosure.

Further, the composition of the present disclosure can significantly inhibit skin inflammatory factors and increase the content of antioxidant enzymes by a small amount.

Based on the above excellent effects, the present disclosure provides use of the composition in the following aspects: preparation of a cosmetic product, preparation of a food and preparation of a medicament.

Among them, the dosage forms of the cosmetic products, foods and medicaments include, but are not limited to, solid preparations (such as solid beverages, powders, capsules, tablets) and liquid preparations (such as oral liquids, beverages).

It can be seen from the above technical solutions that, in the present disclosure, elastin peptide and collagen peptide in a specific molecular weight range are prepared by a specific process, and the composition consists of the two at a suitable ratio can significantly increase the amount of the elastin and collagen in a damaged skin by a small usage, and significantly increase the content of hyaluronic acid and hydroxyproline and decrease the content of MMP3, and at the same time inhibit skin inflammatory factors.

DETAILED DESCRIPTION

The present disclosure discloses a composition of a collagen peptide and an elastin peptide, a method of producing the same and use thereof. Those skilled in the art can implement the present disclosure by learning from the contents of this application and appropriately improving the process parameters. It is to be understood that all such alternatives and modifications are obvious to those skilled in the art and are considered to be included in the present disclosure. The composition of the present disclosure and the method and use thereof have been described by way of examples, and those skilled in the art obviously can change the composition of the present disclosure and the preparation method and application thereof or make appropriate modifications and combinations without departing from the contents, spirit, and scope of the present disclosure, to implement and apply the techniques of the present disclosure.

For the specific examples of the present disclosure involving comparative tests, all the tests are carried out under the same test environments and using the same raw materials except for the distinguishing technical features.

The composition of a collagen peptide and an elastin peptide provided by the present disclosure, method of producing the same and use thereof will be further described below.

Example 1

Preparation of the Composition of the Present Disclosure

Cod skin was chopped and dried in an oven at 80° C. for 12 hours, then pulverized into powders by a pulverizer, and placed in a cool and dry place for use. The cod skin powders was weighed, and water 20-30 times of the weight of the powders was added to make a solution. The solution was heated to 60° C.±5° C., and pepsin 1% amount of the cod skin was added to perform an enzymatic hydrolysis for 4-8 hours. The temperature of the solution was increased to 80±5° C. and then maintained for 0.5-1 hour. The enzymes were inactivated, and then the enzymatic hydrolyzate was passed through a 1 μm filter membrane and the temperature was maintained at 55±5° C. The filtrate was collected and subjected to spray drying to give a collagen peptide. The molecular weight of the collagen was determined by high performance size exclusion chromatography to be 2000-6000 Da.

Bovine ligaments were washed, and 0.5% NaOH solution was added to soak the bovine ligaments at 40-50° C. for 1-2 hours to remove the fats and impurities on the surface. The bovine ligaments were washed to neutral, drained, and minced to obtain a crude extract of elastin. Water 2-4 times of the bovine ligaments was added and the pH was adjusted to 7.5-8.5. Protease Protamex (purchased from Novozymes) 0.4-0.8% amount of the bovine ligaments was added in an amount of. The temperature of the solution was maintained at 60° C. for 6-8 hours, and then increased to 90° C. and maintained for 0.5-1 hour. The enzymes were inactivated, and the enzymatic hydrolyzate was filtered by a plate and frame filter and a 0.45 μm filter membrane. The filtrate was collected to give an elastin peptide solution. After concentrating the filtrate, the filtrate was subjected to powder-sprayed to give an elastin peptide. The molecular weight of the elastin was determined by high performance gel exclusion chromatography to be 300-2000 Da.

The prepared collagen peptide and elastin peptide were compounded into a composition in a weight ratio of (1.6-3.2):(0.075-0.2); the ratio may preferably be (1.6-2.4):0.1, such as 1.6:0.1 (3.2 g collagen peptide+0.2 g elastin peptide) or 2.4:0.1 (4.8 g collagen peptide+0.2 g elastin peptide).

Example 2

Animal Experiment

1. Experimental Materials

D-galactose: purchased from Sigma-Aldrich; Mouse Hyaluronic acid (HA) ELISA kit, Mouse hydroxyproline (Hyp) ELISA kit, Mouse Collagen Type I (Col I) ELISA kit, MMP3 (matrix metalloproteinase 3) ELISA kit, Mouse Elastin ELISA kit, IL-1α ELISA kit and IL-4 kit: purchased from Wuhan Huamei Bioengineering Co., Ltd.; GSH-PX (Glutathione peroxidase): purchased from Nanjing Jiancheng Bioengineering Institute.

2. Experimental Equipment

Electronic Balance: Mettler Toledo, Model: PL303; Skin Moisture Analyzer: Huntkey Portable Elastic Moisture Skin Tester (HUNTKEY JAPAN Co., Ltd.), Model: HKJ-SK03P; UV Sterilization Lamp: Philips Black Light Purple Tube TL-D UV Sterilization Lamp (Philips Lighting Company), Model: TL-D/BLB; Centrifuge: Kylin-Bell Lab Instruments, Model: LX-200; Microplate Reader: BIO-TEK, US, Model: ELX-800; Homogenizer: SONICS MATERIALS INC, Model: VCX 130PB; EP tube, Syringe, etc.

3. Experimental Animals

BALBc-nu nude mice (SPF grade, male, 3-4 weeks old), provided by the Animal Experimental Center of Sun Yat-sen University and housed in the SPF barrier animal room.

4. Experimental Methods

Experimental animal groups and treatment model groups were daily injected subcutaneously with 10% D-gal 1.0 g·kg$^{-1}$ into the nape of the neck, and were UV irradiated with an UV irradiation wavelength of 350-400 nm for 40 min·d$^{-1}$, wherein the light source was about 40 cm vertically from the mice. The modeling was continued for 42 days. The normal control group was daily injected subcutaneously with an equal volume of normal saline into the nape of the neck and housed under normal light. During the experiment, mice were free to food and drink, and the water was changed daily. At the same time of modeling, mice in each sample group were fed with the samples of different dosages for intervention. The samples were diluted proportionally before administration to give the same volume to each group. The administration method was oral lavage feeding once a day for 42 days. The normal group and the model control group were given the same volume of distilled water with the same type of administration method. Group setting: blank group, model group, "A" collagen alone groups (A1: 3.2 g; A2: 6.4 g; A3: 12.8 g), "B" elastin peptide alone groups (B1: 0.2 g; B2: 0.4 g; B3: 0.8 g), "C" collagen peptide+elastin peptide groups (C1: 1.7 g (1.6 g+0.1 g); C2: 3.4 g (3.2 g+0.2 g); C3: 6.8 g (6.4 g+0.4 g));

Three control groups were set up:

Group D1, referred to the process of Example 1, except that the enzymes used were alkaline protease (for collagen peptide, used in an amount 1% of the raw material) and flavor protease (for elastin peptide, used in an amount 0.8% of the raw material), and the weight ratio of the collagen peptide to the elastin peptide was 1.6:0.1, i.e., 3.2 g collagen peptide+0.2 g elastin peptide;

Group D2, referred to the process of Example 1, except that the pore size of the filter membrane was changed, the collagen peptide was filtered by a filter membrane with a pore diameter of 4.0 μm, and the elastin peptide was filtered by a filter membrane with a pore diameter of 2.0 μm, and the weight ratio of the collagen peptide to the elastin peptide was 1.6:0.1, i.e., 3.2 g collagen peptide+0.2 g elastin peptide;

Group D3, referred to the process of Example 2 of patent CN106519020, and the amount of the functional peptide used for composition was 3.4 g;

Type I collagen, elastin, hyaluronic acid, hydroxyproline, MMP3, IL-1α, IL-4, GSH-PX in skin tissue were detected. After blood collection, the mice were sacrificed by cervical dislocation. An area of 1.5 cm×1.5 cm back skin was taken. The rest of the back skin was taken for dry skin measurement of water content and skin histopathological examination. The subcutaneous tissues were cut off and weighed, rinsed with 4° C. 0.9% NaCl solution, dried with paper towels. The skin sample was chopped, and 4° C. 0.9% NaCl solution (the total volume of 0.9% NaCl solution was 9 times the weight of the skin) and an appropriate amount of protein lysis buffer were added. The skin sample was homogenized with a tissue homogenizer (on ice, 10 s each time, 30 s interval, repeating 5-6 times). The homogenate was centrifuged at 3,000 r/min at 4° C. for 15 min. An appropriate amount of supernatant was collected and subjected to tests according to the instructions of the ELISA kits to measure the activity of type I collagen, elastin, hyaluronic acid, hydroxyproline, MMP3, IL-1α, IL-4, and GSH-PX in the skin tissue.

5. Statistical Analysis

The experimental data were statistically processed by GraphPad Prism 6.0 biostatistics software: the measurement data were expressed as mean±standard deviation (mean±SD), analyzed by variance analysis combined with Dunnett's multiple comparison method; the data were analyzed by Kruskal-Wallis rank sum test.

6. Results (1) Collagen

As shown in Table 1, type I collagen content in the skin of the nude mice of the model group was significantly lower than that in the blank group (P<0.001); in A3 group using collagen peptide alone and B3 group using elastin peptide alone, type I collagen in the skin was significantly increased as compared with the model group (P<0.001), but the use amounts were relatively high; in C2 group of the composition of the present disclosure, though the use amount was a quarter of the total amount of A3 group+B3 group, type I collagen in the skin was significantly increased as compared with the model group (P<0.01); in C3 group of the composition of the present disclosure, though used in a half of the total amount of A3 group+B3 group, type I collagen in the skin was significantly increased as compared with the model group (P<0.001). The results demonstrate that the compositions of the present application possess significantly synergistic effects.

In the three control groups, by adjusting the type of enzymes and the pore size of the filter membrane, both of D1 and D2 groups did not significantly increase the collagen amount; although D3 group significantly increased the collagen amount, the amount of elastin was not significantly increased.

TABLE 1

| Groups | Collagen I (IOD) | Elastin (IOD) |
|---|---|---|
| Blank group | 5228 ± 146*** | 5044 ± 141*** |
| Model group | 2777 ± 63 | 2585 ± 242 |
| A1 | 2855 ± 39 | 2051 ± 39 |
| A2 | 3361 ± 60 | 3088 ± 432 |
| A3 | 4774 ± 167*** | 3206 ± 75 |
| B1 | 2822 ± 163 | 2749 ± 209 |
| B2 | 3373 ± 144 | 3530 ± 254 |
| B3 | 3808 ± 94*** | 4360 ± 315** |
| C1 | 2887 ± 116 | 3144 ± 23 |
| C2 | 3653 ± 205** | 3630 ± 282** |
| C3 | 4925 ± 47*** | 4877 ± 64*** |
| D1 | 3263 ± 174 | 3430 ± 214 |
| D2 | 3423 ± 251 | 3390 ± 152 |
| D3 | 3723 ± 209** | 3360 ± 174 |

Note:
*P < 0.05, P < 0.01, *P < 0.001 as compared with the model group (2) Elastin As shown in Table 1, the elastin content in the skin of the nude mice of the model group was significantly lower than that of the blank group (P<0.001); in neither of A1-3 groups using collagen peptide alone and B1-2 groups using elastin peptide alone, the elastin content in the skin of the nude mice was significantly increased as compared with the model group, especially in the A1 group using collagen peptide alone, the elastin content decreased instead; in B3 group using elastin peptide alone, the elastin in the skin was significantly increased (P<0.0001), but the use amount was relatively high, up to 0.8 g; in C3 group of the composition of the present disclosure, although the use amount was a half of the total amount of A3 group+B3 group, which was the same as the total amount of A2 group+B2 group, the elastin in the skin was significantly increased as compared with the model group (P<0.001). The results demonstrate that the compositions of the present disclosure possess significantly synergistic effects.

In the three control groups, by adjusting the type of enzymes and the pore size of the filter membrane, both of D1 and D2 groups did not significantly increase the elastin amount; D3 group did not significantly increase the elastin amount either.

(3) MMP3, Hyaluronic Acid, Hydroxyproline

As shown in Table 2, as compared with the blank group, the contents of MMP3, hyaluronic acid and hydroxyproline in the skin of the nude mice of the model group were significantly different (P<0.001); in A1-3 groups using collagen peptide alone and B1-3 groups using elastin peptide alone, the contents of MMP3, hyaluronic acid and hydroxyproline in the skin of the nude mice were significantly changed as compared with the model group (P<0.05; P<0.01), but the use amount was relatively high; in C2 group of the composition of the present disclosure, though the use amount was a quarter of the total amount of A3 group+B3 group, the contents of MMP3, hyaluronic acid and hydroxyproline were significantly changed in the skin of the nude mice as compared with the model group (P<0.05); in C3 group of the composition of the present disclosure, though the use amount was a half of the total amount of A3 group+B3 group, the contents of MMP3, hyaluronic acid and hydroxyproline in the skin of the nude mice were significantly changed as compared with the model group (P<0.01; P<0.001). The results demonstrate that the compositions of the present disclosure possess significantly synergistic effects.

Although D1-D3 groups significantly increased the amount of hyaluronic acid, they did not achieve the intended purpose of increasing the amount of hydroxyproline and decreasing the amount of MMP3.

TABLE 2

Results of ELISA kit detection

| Groups | MMP3 (ng/mg) | Hyaluronic acid (pg/mg) | Hydroxyproline (ng/mg) |
|---|---|---|---|
| Blank group | 121.51 ± 21.45*** | 232.09 ± 11.31*** | 28.13 ± 7.16** |
| Model group | 265.50 ± 36.21 | 121.23 ± 19.51 | 15.22 ± 7.36 |
| A1 | 251.71 ± 32.23 | 132.34 ± 11.32 | 14.65 ± 1.23 |
| A2 | 240.50 ± 55.67 | 161.00 ± 10.81* | 14.25 ± 4.23 |
| A3 | 196.25 ± 22.11** | 189.20 ± 13.11** | 16.81 ± 2.23* |
| B1 | 271.73 ± 15.15 | 129.14 ± 16.31 | 15.21 ± 0.22 |
| B2 | 231.50 ± 12.65 | 145.21 ± 15.23* | 15.28 ± 4.99 |
| B3 | 190.33 ± 18.21** | 179.11 ± 12.95** | 17.19 ± 1.54* |
| C1 | 241.78 ± 11.26 | 121.12 ± 19.52 | 16.11 ± 1.02 |
| C2 | 221.32 ± 12.55* | 169.01 ± 11.63* | 16.99 ± 3.90* |
| C3 | 161.12 ± 21.66*** | 190.94 ± 20.13** | 19.16 ± 0.54** |
| D1 | 240.50 ± 55.67 | 161.00 ± 10.81* | 14.25 ± 4.23 |
| D2 | 231.50 ± 12.65 | 145.21 ± 15.23* | 15.28 ± 4.45 |
| D3 | 240.50 ± 55.67 | 162.00 ± 10.81* | 15.25 ± 3.23 |

Note:
*P < 0.05, P < 0.01, *P < 0.001 as compared with the model group;

(4) Skin Inflammatory Factors

As shown in Table 3, as compared with the blank group, contents of inflammatory factor IL-1α and IL-4 in the skin of the nude mice of the model group were significantly increased, while content of GSH-Px was significantly decreased; although in A1-3 groups using collagen peptide alone and B1-3 groups using elastin peptide alone, one or more of the above indicators were significantly increased, the composition of the present disclosure also has a significant improvement in its one-quarter or one-half amount. The results demonstrate that the compositions of the present disclosure possess significantly synergistic effects.

D1-D3 groups can only improve the content of IL-1α inflammatory factor, but not for the two other indexes, which was obviously inferior to the effect of improving the various inflammatory factors indexes by the present disclosure.

TABLE 3

Results of ELISA kit detection

| Groups | IL-1α (pg/ml) | IL-4 (pg/ml) | GSH-Px (ng/L) |
|---|---|---|---|
| Blank group | 94.67 ± 2.45*** | 255.02 ± 9.31*** | 265.93 ± 2.11*** |
| Model group | 130.41 ± 3.41 | 287.35 ± 3.11 | 194.46 ± 2.17 |
| A1 | 129.28 ± 3.29* | 288.60 ± 6.14 | 193.99 ± 1.98 |
| A2 | 128.38 ± 5.17* | 279.71 ± 11.21 | 198.88 ± 4.12* |
| A3 | 104.94 ± 1.23*** | 256.46 ± 3.27** | 198.68 ± 2.34 |
| B1 | 128.81 ± 3.34* | 284.48 ± 6.26 | 195.04 ± 1.45 |
| B2 | 117.80 ± 2.43*** | 282.65 ± 5.21 | 194.71 ± 2.67 |
| B3 | 96.97 ± 2.43*** | 276.29 ± 4.11** | 199.74 ± 2.21* |
| C1 | 129.98 ± 1.18* | 283.96 ± 2.26 | 197.40 ± 3.11* |
| C2 | 129.67 ± 3.15* | 287.29 ± 9.11 | 197.46 ± 4.09* |
| C3 | 114.15 ± 2.23*** | 279.98 ± 7.25** | 196.68 ± 1.34* |
| D1 | 129.28 ± 3.29* | 281.60 ± 4.42 | 192.93 ± 1.87 |
| D2 | 129.28 ± 3.29* | 282.60 ± 5.44 | 194.99 ± 1.58 |
| D3 | 128.97 ± 2.45* | 283.40 ± 4.12 | 196.44 ± 1.68 |

Note:
*$P < 0.05$, $P < 0.01$, *$P < 0.001$ as compared with the model group The above are merely preferred embodiments of the present disclosure. It should be noted that one of ordinary skill in the art can also make several improvements and refinements without departing from the principles of the present disclosure. These improvements and refinements should also be regarded as the scope of protection of the present disclosure.

What is claimed is:

1. A method of producing a composition of a collagen peptide and an elastin peptide, comprising:
   performing enzymatic hydrolysis of the collagen material with pepsin or trypsin, passing the enzymatic hydrolysate through a 1 to 2 μm filter membrane, and subjecting the filtrate to spray drying to obtain the collagen peptide;
   removing fats and impurities on the surface of a material containing elastin, performing enzymatic hydrolysis of the material containing elastin with papain and/or Bacillus protease, passing the enzymatic hydrolysate through a 0.45 to 1 μm filter membrane, and subjecting the filtrate to spray drying to obtain the elastin peptide; and
   mixing the collagen peptide and the elastin peptide to obtain the composition.

2. The method according to claim 1,
   wherein prior to enzymatic hydrolysis of the material containing collagen, drying and pulverizing the material containing collagen and wherein the enzymatic hydrolysis step comprises adding water and pepsin or trypsin in an amount equal to 1% of the amount of the collagen material to perform enzymatic hydrolysis, passing the enzymatic hydrolysate through a 1 to 2 μm filter membrane, and subjecting the filtrate to spray drying to obtain the collagen peptide; and
   wherein the removing fats and impurities from the surface of a material of a material containing elastin is performed by soaking the material containing elastin with a NaOH solution, wherein prior to the enzymatic hydrolysis step comprises washing and mincing the material containing elastin, and adding water and adjusting pH to 7.5 to 8.5, wherein the enzymatic hydrolysis step comprises adding papain and/or Bacillus protease at an amount equal to 0.4-0.8% of the amount of the material containing elastin to perform enzymatic hydrolysis, wherein the filtering step comprises filtering the enzymatic hydrolysate by a plate and frame filter and a 0.45 to 1 μm filter membrane, and subjecting the filtrate to spray drying after concentrating to obtain the elastin peptide; and
   mixing the collagen peptide and the elastin peptide to obtain the composition.

3. The method according to claim 2,
   wherein prior to the drying step, the material containing collagen is subjected to chopping; wherein the drying step comprises drying in an 80° C. oven for 12 hours, wherein after pulverizing, the powder is reconstituted by adding water in an amount 20 to 30 times the amount of the powder, heating the resulting solution to a temperature of 60° C.±5° C., adding pepsin or trypsin in an amount equal to 1% of the amount of the solution to perform enzymatic hydrolysis for 4 to 8 hours, increasing the temperature to 80° C.±5° C. and maintain the temperature for 0.5 to 1 hour, inactivating the enzyme, passing the enzymatic hydrolyzate through a 1 to 2 μm filter membrane, maintaining the temperature at 55±5° C. during filtration, and subjecting the filtrate to spray drying to obtain the collagen peptide;
   wherein prior to the removal step, washing the material containing elastin, wherein the soaking step comprises adding a 0.5% NaOH solution and soaking the material containing elastin at 40° C. to 50° C. for 1 to 2 hours to remove fats and impurities on the surface of the material containing elastin, wherein the washing step comprises washing the material containing elastin until a neutral pH is obtained then draining and mincing the material containing elastin to obtain a crude extract of elastin, wherein the adding water method steps requires adding water in an amount 2 to 4 times the amount of the material containing elastin and adjusting pH to 7.5 to 8.5, adding papain and/or Bacillus protease at an amount equal to 0.4-0.8% of the amount of the material containing elastin to perform enzymatic hydrolysis, maintaining the temperature at 60° C. for 6 to 8 hours, increasing the temperature to 90° C. and maintaining the temperature for 0.5 to 1 hour, inactivating the enzyme, filtering the enzymatic hydrolysate by a plate and frame filter and a 0.45 to 1 μm filter membrane, collecting the filtrate to obtain a solution comprising elastin peptide, and subjecting the solution to spray drying after concentrating the solution to obtain the elastin peptide; and
   mixing the collagen peptide and the elastin peptide to obtain the composition.

4. The method according to claim 1, wherein the mass ratio of the collagen peptide to the elastin peptide is 1.6:0.1-2.4:0.1.

* * * * *